United States Patent [19]  [11] Patent Number: 4,969,115
Rosenthal  [45] Date of Patent: Nov. 6, 1990

[54] METHOD AND APPARATUS FOR IDENTIFYING CAUSES OF REPEATABILITY PROBLEMS IN NEAR INFRARED ANALYTICAL INSTRUMENTS

[75] Inventor: Robert D. Rosenthal, Gaithersburg, Md.

[73] Assignee: Futrex Inc., Gaithersburg, Md.

[21] Appl. No.: 274,836

[22] Filed: Nov. 23, 1988

[51] Int. Cl.$^5$ .............................................. G12B 13/00
[52] U.S. Cl. ................................ 364/571.03; 364/498; 250/252.1
[58] Field of Search ...................... 364/571.05, 571.03, 364/557, 556, 498; 250/339, 341, 252.1 A

[56] References Cited

U.S. PATENT DOCUMENTS 3,961,898  6/1976  Neeley et al. ........................ 364/498
4,466,076  8/1984  Rosenthal ......................... 364/571.03
4,627,008  12/1986 Rosenthal ............................ 364/550
4,766,551  8/1988  Begley ................................. 364/498

OTHER PUBLICATIONS

Characteristics of Non-Destructive Near-Infrared Instruments for Gain and Food Products, 1985 Meeting Japan Food Science Institute, by R. D. Rosenthal, Trebor Industries, pp. 1-23.

Primary Examiner—Parshotam S. Lall
Assistant Examiner—S. A. Melnick
Attorney, Agent, or Firm—Bernard, Rothwell & Brown

[57] ABSTRACT

A method and apparatus for determining whether a subsequent sample is substantially identical to an initial sample in a near infrared quantitative analysis instrument. An initial sample is measured for a plurality of characteristics which include the ambient temperature of the analysis instrument at the time of reading, the temperature of the sample itself, the optical energy level of the sample, the moisture content of the sample, and the percent protein of the sample. These characteristics are stored in a computer to provide a series of comparison criteria. A subsequent sample is then measured for the same characteristics as the initial sample and these characteristics are compared to the comparison criteria to determine if the subsequent sample is substantially identical to the previous sample. The subsequent sample is determined to be substantially identical to the initial sample for a given criterion if the subsequent sample's measurement for the corresponding characteristic is within a tolerance for that criterion. If the subsequent sample is judged to be substantially identical to the initial sample for all criteria, it is determined to be substantially identical to the initial sample.

8 Claims, 3 Drawing Sheets

METHOD AND APPARATUS FOR IDENTIFYING CAUSES OF REPEATABILITY PROBLEMS IN NEAR INFRARED ANALYTICAL INSTRUMENTS

BACKGROUND OF THE INVENTION

1. Field of the Invention

The present invention relates to the field of near infrared analytical instruments for measuring constituents of materials.

2. Description of the Background Art

The prior art contains a number of devices and processes for measuring constituents of samples such as grains. Such devices are known which measure moisture, protein and oil content utilizing near infrared radiation energy. For example, U.S. Pat. Nos. 4,466,076 and 4,627,008, both to Robert D. Rosenthal, the inventor of the present invention, disclose instruments that can measure constituents of a sample by transmitting near infrared radiation energy through the samples. These near infrared quantitative analysis instruments utilize a phenomenon that certain organic substances absorb energy in the near infrared region of the spectrum. In use, there are certain circumstances under which these instruments do not appear to provide good repeatability, i.e., the ability of the instrument to confirm the reading between subsequent and initial samples from a single batch. Because repeatability generally is checked only at the point of read-out, it is difficult to tell what factors are causing repeatability problems. Identifying repeatability problems can therefore be somewhat difficult. There thus exists a need for a device and method for indicating to a user what factors are causing any repeatability problems which may occur.

SUMMARY OF THE INVENTION

The present invention provides a near infrared analytical instrument with the ability to indicate whether a particular sample is substantially identical to a previously analyzed sample. The analytical instrument measures a number of characteristics of the initial sample, such as the ambient temperature of the instrument at the time measurements are taken of the initial sample, the temperature of the initial sample, the optical energy level of the initial sample, the moisture content of the initial sample, and the percent protein of the initial sample. The measurements of these characteristics are stored in a computer to create a series of comparison criteria values. A subsequent sample is then measured for the same characteristics as the initial sample and the values for these characteristics are compared to the comparison criteria values of the initial sample to determine if the subsequent sample is substantially identical to the initial sample. The subsequent sample is judged to be substantially identical to the initial sample for a given criterion if the value of the subsequent sample's measurement for the corresponding characteristic is within a predetermined tolerance for that criterion. The comparison criteria determine whether the subsequent sample is substantially identical to the initial sample. If the subsequent sample fails any one of the comparison criteria of the initial sample, it is determined not to be sufficiently identical to the initial sample. If judged to be substantially identical for all criteria, it is determined to be sufficiently identical to the initial sample to provide good repeatability.

DETAILED DESCRIPTION OF THE INVENTION

The present invention is applicable to near infrared quantitative analysis instruments, such as those utilizing the principals of transmittance, interactance or reflectance. Such instruments are capable of determining various characteristics of a sample, such a percent moisture, protein and oil, based on near infrared radiation absorption at particular wavelengths, see, e.g., the previously mentioned U.S. Pat. Nos. 4,466,076 and 4,627,008, incorporated herein by reference.

Figure 1:
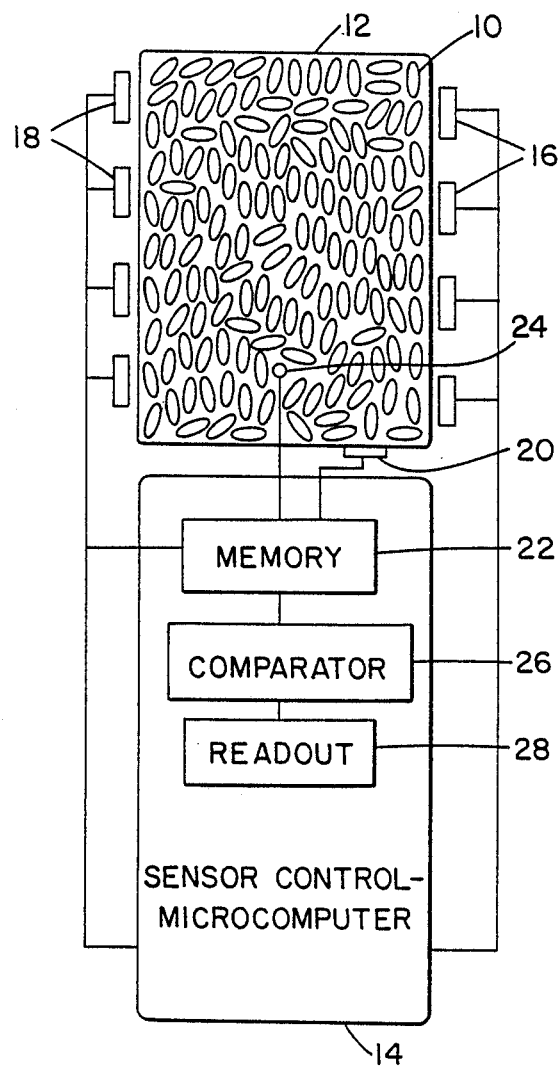
FIG. 1 is a schematic illustration of an apparatus according to the present invention.

In the near infrared transmittance instrument shown schematically in FIG. 1, a sample 10 is contained within a sample holder 12 for near infrared quantitative analysis. Under the control of sensor control/microcomputer 14, near infrared radiation is emitted from infrared-emitting diodes (IREDs) 16. The near infrared radiation passes through a near infrared-transparent wall portion of sample holder 12 and irradiates the sample being analyzed. When the near infrared radiation emitted from IREDs 16 irradiates the sample being analyzed, a certain portion of the energy is transmitted through the sample while some of the energy is absorbed by the sample. For convenience, four IREDs 16 are schematically shown although more or less can be used. In preferred instruments, twelve IREDs are sequentially operated to determine the near infrared absorption characteristics of the sample.

Energy passing through the sample is measured by near infrared radiation detectors 18 at a plurality of wavelengths in order to determine the absorption characteristics of the sample, which can be utilized to determine the moisture, protein and oil content of the sample, as is known in the art.

By the present invention, the causes of repeatability problems between subsequent and initial samples from a single batch can be identified.

The causes of repeatability problems are identified in accordance with the present invention by obtaining a plurality of comparison criteria values for an initial sample. The characteristics that are measured for the initial sample are selected from the group consisting of ambient temperature of the measuring instrument at the time of measuring the initial sample's characteristics, the temperature of the initial sample per se, the optical energy level of the initial sample, the moisture content of the initial sample, and the percent protein of the initial sample. In accordance with one embodiment, at least three of the above-noted characteristics are measured. In more preferred embodiments, at least four of these characteristics are measured, and in the most preferred embodiment, all five of the listed characteristics are measured in order to identify repeatability problems, if they exist. If desired, characteristics other than those listed above can also be measured.

The measured comparison criteria values of the initial sample are stored in memory 22 of sensor control/microcomputer 14, and a corresponding plurality of comparison values are obtained for a subsequently analyzed sample by measuring a corresponding plurality of the characteristics listed above. The characteristic values measured of the subsequent sample then are compared to the corresponding characteristic values measured for the initial sample in order to determine whether or not the subsequent sample is substantially identical to the initial sample.

Figure 3:
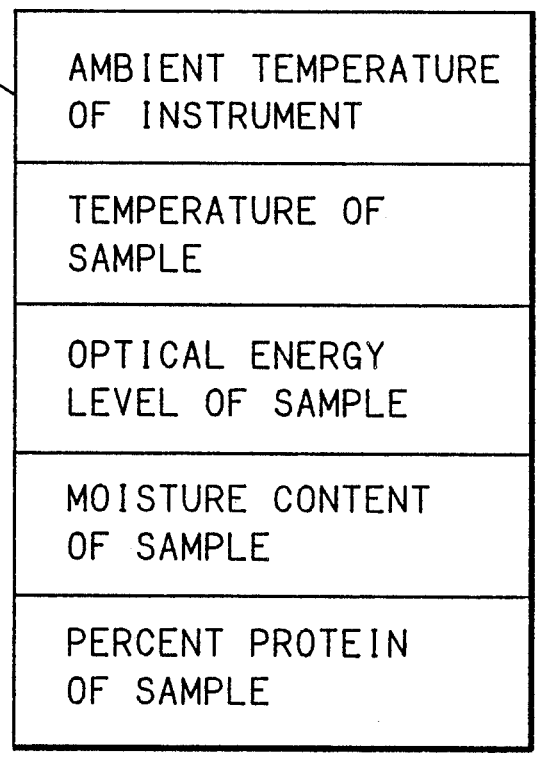
FIG. 3 is a schematic illustration of the sensor control/microcomputer memory used in accordance with the present invention.

In an instrument as schematically shown in FIG. 1, the ambient temperature of the instrument at the time of analysis is measured by thermistor 20 and the value is stored in memory 22 of sensor control/microcomputer 14 and as further illustrated in FIG. 3.

The sample temperature is taken by thermistor 24, and its value is stored in memory 22 of sensor control/microcomputer 14 as shown in FIGS. 1 and 3.

The sample moisture content is determined by the near infrared radiation absorption characteristics of the sample, as is known in the art, and the percent moisture by weight for the sample is stored in memory 22 of sensor control/microcomputer 14 as shown in FIGS. 1 and 3.

Similarly, the percent protein of a sample is determined by the near infrared radiation absorption characteristics of the sample as is known in the art, and the value of the percent protein is stored in memory 22 of microcomputer 14 as shown in FIGS. 1 and 3.

The overall optical energy level of a sample is determined by taking the summation of the optical density measurements for each of detectors 18. This optical energy level value is stored in memory 22 of sensor control/microcomputer 14 as shown in FIGS. 1 and 3.

Figure 2:
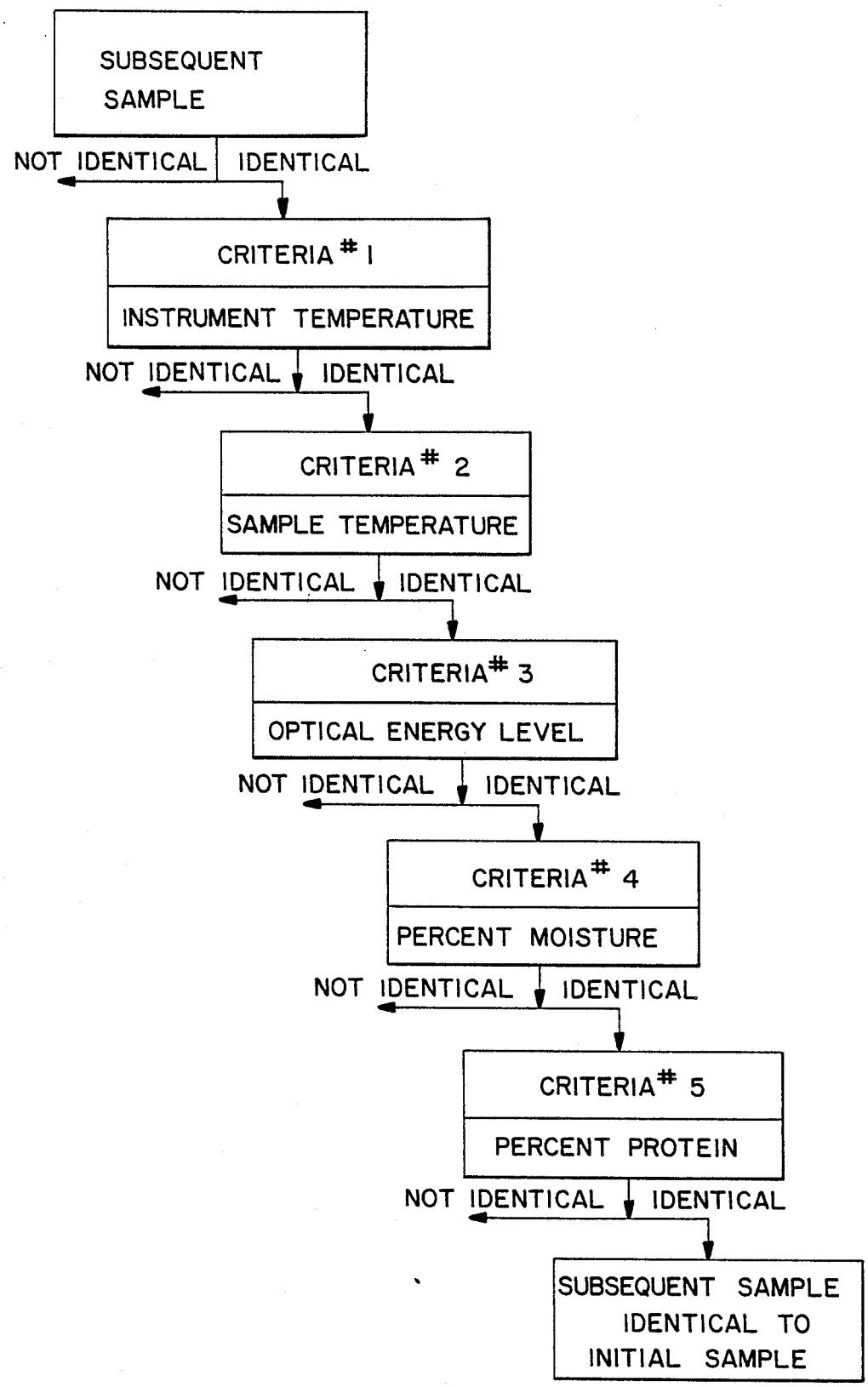
FIG. 2, is a flow chart showing how a subsequent sample is compared to an initial sample via successive criteria in accordance with one embodiment of the present invention.

The stored measurements for a particular initial sample become the criteria to which the measurements of a subsequently measured sample are compared. There is a tolerance range for each criterion which the subsequent sample must fall within in order to be determined by the instrument to be substantially identical to a previous sample. FIG. 2 illustrates a flow chart of how a comparison between two samples may be carried out according to one embodiment of the invention.

Since a change in the instrument's temperature may cause repeatability problems, the ambient temperature of the instrument measured by thermistor 20 at the time the measurements are made on the subsequent sample is compared by comparator 26 to the recorded ambient temperature of the instrument at the time the measurements were made on the initial sample. If the ambient temperature at the time measurements are made on the subsequent sample is within the tolerance of the ambient temperature measurement for the initial sample, the subsequent sample is judged to be substantially identical for this criterion. If the subsequent sample fails this criterion, the instrument determines that the subsequent sample is different from the initial sample, and indicates so on readout 28. In preferred embodiments, the tolerance for the ambient temperature criterion is about $\pm 0.5°$ F.

A change in a sample's temperature may cause repeatability problems. Accordingly, comparator 26 determines whether the temperature of the subsequent sample, as measured by thermistor 24, is within the tolerance of the initial sample's temperature measurement stored in memory 22. If the subsequent sample is within the tolerance of the temperature of the initial sample, then the subsequent sample is judged to be identical for this criterion. If it is not within the tolerance, the instrument determines that the subsequent sample is different from the initial sample, and so indicates on readout 28. In preferred embodiments, the tolerance for the sample temperature criterion is about $\pm 2°$ F.

Similarly, the optical energy level of the subsequent sample can be compared to the optical energy level of initial sample to determine if the samples are substantially the same. As noted above, the optical energy level of a sample is determined by taking the summation of the optical density measurements for all detectors 18 during the analysis. If the summation of these optical density measurements for a subsequent sample is within the tolerance of the sum of the corresponding optical density measurements for the previous sample, the subsequent sample will be judged to be substantially identical to the previous sample for this criterion. If it is not within this tolerance, the comparator 26 determines that the subsequent sample is different, and an appropriate readout is given. A preferred tolerance for the optical density criterion is about $\pm 0.5\%$.

Another valuable criterion is moisture content of the sample, which can be determined by measuring near infrared absorption by the sample according to known techniques. In preferred embodiments, the subsequent sample's moisture content is compared to the moisture content of the initial sample. If the subsequent sample's moisture content is within the tolerance of the moisture content measurement for the initial sample, the comparator determines that the subsequent sample is substantially identical to the initial sample for this criterion. If the subsequent sample is not within this tolerance, it determines that the subsequent sample is different and provides a readout. In preferred embodiments, the tolerance for the moisture content criterion is about $\pm 0.5\%$.

In preferred embodiments, the percent protein of the subsequent sample, determined by measuring near infrared absorption by the sample according to known techniques, is compared to the percent protein of the initial sample. If the percent protein of the subsequent sample is within the tolerance of the percent protein measurement for the initial sample, the comparator determines that the subsequent sample is substantially identical to the initial sample for this criterion. If the percent protein of the subsequent sample is outside the tolerance range, readout 28 indicates that the subsequent sample is different from the initial sample. A preferred tolerance for the percent protein criterion is about $\pm 0.6\%$.

In particularly preferred embodiments, if the subsequent sample has satisfied all the selected criteria, the instrument provides a percent protein readout for the subsequent sample which is an average of the percent protein stored for the initial sample and the percent protein measured for the subsequent sample.

In addition to the above-mentioned criteria, other criteria may also be used. If desired, the instrument can include a timer that negates the use of the successive criteria if a certain amount of time, e.g., five minutes, has passed between readings of the new sample and the initial sample, after which the instrument assumes that the sample being read is a new sample.

What is claimed is:

1. A method for determining whether a subsequent sample is substantially identical to an initial sample in a near infrared radiation analysis comprising the steps of irradiating the initial and subsequent samples with near infrared radiation in a near infrared analysis instrument and measuring optical densities of said samples, the method further comprising the steps of:

(a) obtaining a plurality of comparison criteria values for the initial sample by measuring a plurality of characteristic values from the following: ambient temperature of said instrument at time of measuring the initial sample's characteristics, the temperature of the initial sample, the optical energy level of the initial sample, the moisture content of the initial sample, and the percent protein of the initial sample;

(b) storing the comparison criteria values of the initial sample;

(c) measuring a plurality of characteristic values of a subsequent sample which correspond to characteristics measured by the initial sample, said plurality of characteristics of the subsequent sample being obtained from the following: ambient temperature of said instrument at time of measuring the subsequent sample's characteristics, the temperature of the subsequent sample, the optical energy level of the subsequent sample, the moisture content of the subsequent sample, and the percent protein of the subsequent sample; and (d) comparing the characteristic values measured for the subsequent sample to the corresponding characteristic values measured for the initial sample in order to determine whether or not the subsequent sample is substantially identical to the initial sample.

2. The method of claim 1 wherein one of the characteristic values that is measured on the initial sample and the subsequent sample is percent protein, the method further including the steps of averaging the measured percent protein values for the initial sample and the subsequent sample and providing a readout of said average.

3. The method of claim 1, wherein one of the characteristic values that is measured of the initial sample and the subsequent sample is ambient temperature of the instrument, wherein an ambient instrument temperature for the subsequent sample within about ±0.5° F. of the ambient instrument temperature of the initial sample indicates that the ambient instrument temperatures for both the initial sample and the subsequent sample are substantially identical.

4. The method of claim 1, wherein one of the characteristic values that is measured of the initial sample and the subsequent sample is sample temperature of the initial sample and the subsequent sample, wherein a measured sample temperature for the subsequent sample within about ±2° F. of the measured sample temperature of the initial sample indicates that the sample temperatures for both the initial sample and the subsequent sample are substantially identical.

5. The method of claim 1, wherein one of the characteristic values that is measured of the initial sample and the subsequent sample is optical energy level, wherein an optical energy level for the subsequent sample within about ±0.5% of the optical energy level of the initial sample indicates that the optical energy levels of both the initial sample and the subsequent sample are substantially identical.

6. The method of claim 1, wherein one of the characteristic values that is measured of the initial sample and the subsequent sample is moisture content, wherein percent moisture of the subsequent sample within about 0.5% by weight of the moisture content of the initial sample indicates that the moisture contents of both the initial sample and the subsequent sample are substantially identical.

7. The method of claim 1 wherein one of the characteristic values that is measured of the initial sample and the subsequent sample is percent protein, wherein a percent protein of the subsequent sample within about 0.6% by weight of the percent protein of the initial sample indicates that the percent protein of both the initial and the subsequent sample is substantially identical.

8. An apparatus for determining whether a subsequent sample is substantially identical to an initial sample comprising a near infrared analysis instrument having means for irradiating a sample with near infrared radiation and means for measuring the optical density of said sample, the apparatus further including:

(a) means for obtaining a plurality of comparison criteria values for a sample by measuring a plurality of characteristics from the following: ambient temperature of said instrument at time of measuring the initial sample's characteristics, the temperature of the initial sample, the optical energy level of the initial sample, the moisture content of the initial sample, and the percent protein of the initial sample;

(b) means for storing measurements of a plurality of said characteristics made by the measuring means for an initial sample;

(c) means for comparing measurements made for a subsequent sample with said measurements of a corresponding plurality of said characteristics made for the initial sample; and (d) means for indicating whether the subsequent sample is substantially identical to the initial sample based on the comparison of measurements made for the initial and subsequent samples.

* * * * *